(12) United States Patent
Goldowsky (10) Patent No.: US 6,190,319 B1
(45) Date of Patent: Feb. 20, 2001

(54) SELF CALIBRATING LINEAR POSITION SENSOR

(75) Inventor: Michael Philip Goldowsky, Valhalla, NY (US)

(73) Assignee: International Business Machines Corporation, Armonk, NY (US)

( * ) Notice: Under 35 U.S.C. 154(b), the term of this patent shall be extended for 0 days.

(21) Appl. No.: 09/334,504

(22) Filed: Jun. 21, 1999

(51) Int. Cl.[7] .................................................. A61B 8/00
(52) U.S. Cl. ................................................ 600/437; 600/16
(58) Field of Search .............................. 600/16, 17, 437, 600/443, 447, 449; 73/618, 619, 625, 626; 436/68; 324/227

(56) References Cited

U.S. PATENT DOCUMENTS

| | | | |
|---|---|---|---|
| 4,576,035 | * | 3/1986 | Hooven et al. ........................... 73/4 |
| 5,485,845 | * | 1/1996 | Verdonk et al. ...................... 600/462 |
| 5,730,136 | * | 3/1998 | Laufer et al. ........................... 73/633 |
| 5,878,380 | * | 3/1999 | Hollandsworth ..................... 702/159 |
| 5,924,975 | * | 7/1999 | Goldowsky ............................. 600/16 |
| 6,027,445 | * | 2/2000 | Von Bahr .............................. 600/309 |

* cited by examiner

*Primary Examiner*—Marvin M. Lateef
*Assistant Examiner*—Ali M. Imam
(74) *Attorney, Agent, or Firm*—Francis L. Conte (57) ABSTRACT

A rotor is disposed coaxially in a tubular housing and spaced therefrom to define a gap for receiving a fluid. An ultrasonic transducer is mounted at one end of the housing in alignment with a target at a corresponding end of the rotor. Ultrasonic pulses are bounced off the target for measuring linear position thereof based on the speed of sound in the fluid and round trip pulse time between the transducer and target. The speed of sound in the fluid between the transducer and target is self-calibrated.

23 Claims, 5 Drawing Sheets

SELF CALIBRATING LINEAR POSITION SENSOR

BACKGROUND OF THE INVENTION

The present invention relates generally to a rotor supported in a housing, and, more specifically, to measuring axial or linear position thereof.

In U.S. patent application Ser. No. 08/686,618, filed Jul. 19, 1996, now U.S. Pat. Ser. No. 5,924,975 a linear pump is described for pumping blood as a left ventricular assist device (LVAD) for a human patient. The pump includes a tubular piston inside a tubular housing with a pair of check valves cooperating therewith for pumping blood therethrough as the piston reciprocates in the housing.

Reciprocation is effected by incorporating a linear motor having axially adjoining stator drive coils disposed in the housing which cooperate with a pair of axially spaced apart permanent magnet rings disposed in the piston. A linear position sensor is located in the housing for detecting axial position of the piston for use in commutating or controlling piston movement in pumping the blood.

An exemplary position sensor is in the form of a magneto resistor which cooperates with grooves machined in the outer diameter of the piston. In the presence of a magnetic field, the resistance of the magneto resistor increases dramatically and may be used to detect the grooves in the piston to thereby determine piston axial position in the housing for commutating the drive coils.

In the preferred embodiment of the linear pump, the piston also rotates in the housing to develop a journal bearing therebetween in which the blood fluid is pressurized in the journal bearing gap or annulus to suspend the piston and prevent contact with the housing bore.

In a further development of the pump, a rotary position encoder is used to measure the rotation angle of the piston for controlling its rotation during operation. A non-contact rotary encoder uses a Hall effect magnetic field sensor to detect the rotary position of the piston. However, the magneto resistor linear position sensor and the Hall effect rotary encoder are incompatible with each other since they both depend on magnetic fields.

Accordingly, it is desired to provide a linear position sensor unaffected by magnetic fields.

BRIEF SUMMARY OF THE INVENTION

A rotor is disposed coaxially in a tubular housing and spaced therefrom to define a gap for receiving a fluid. An ultrasonic transducer is mounted at one end of the housing in alignment with a target at a corresponding end of the rotor. Ultrasonic pulses are bounced off the target for measuring linear position thereof based on the speed of sound in the fluid and round trip pulse time between the transducer and target. The speed of sound in the fluid between the transducer and target is self-calibrated.

BRIEF DESCRIPTION OF THE DRAWINGS

The invention, in accordance with preferred and exemplary embodiments, together with further objects and advantages thereof, is more particularly described in the following detailed description taken in conjunction with the accompanying drawings in which.

DETAILED DESCRIPTION OF THE INVENTION

Figure 1:
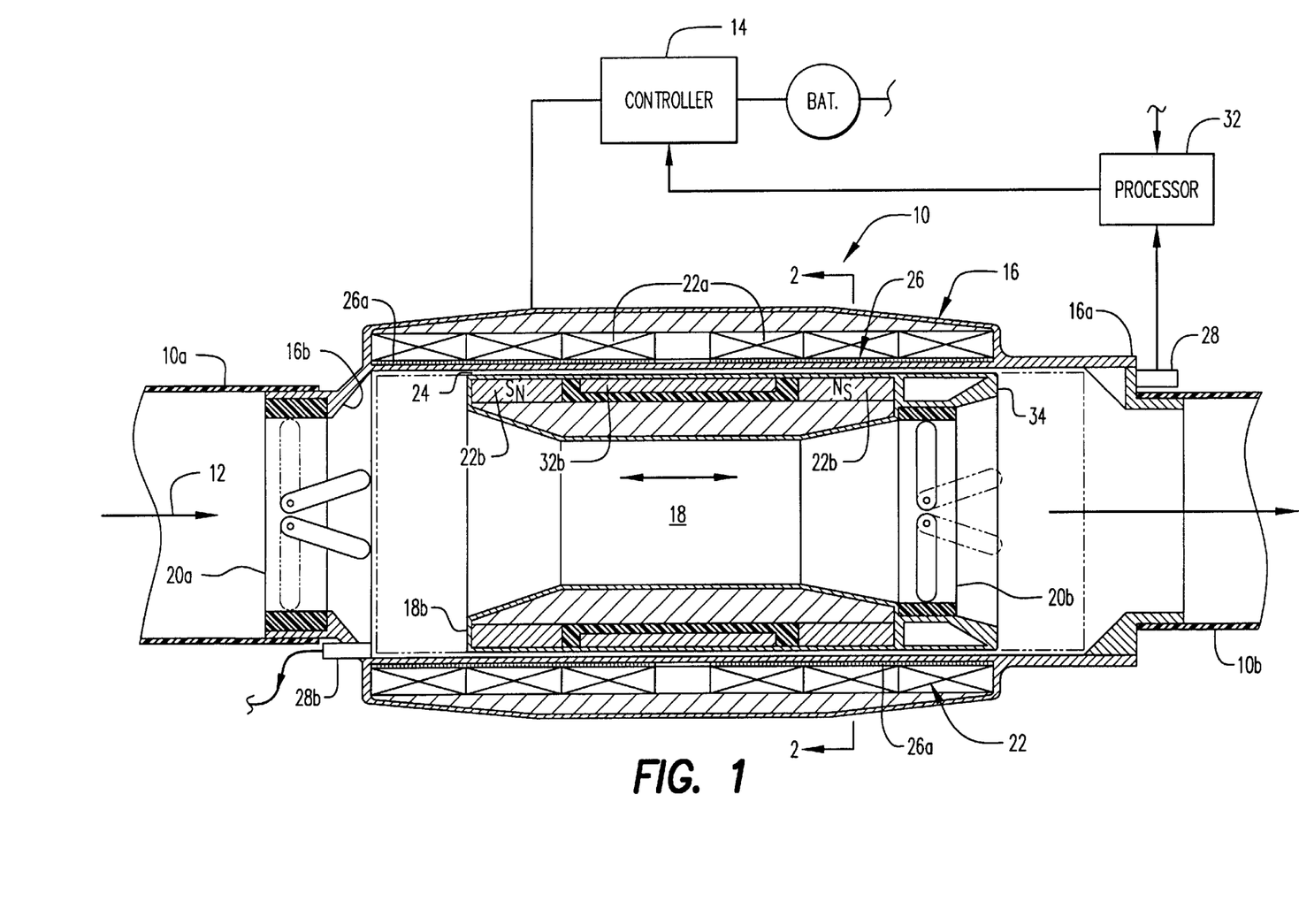
FIG. 1 is an axial, partly sectional view of a linear pump having a self-calibrating ultrasonic linear position sensor for measuring position of a reciprocating piston in a housing in accordance with an exemplary embodiment of the present invention.

Illustrated in FIG. 1 is a linear pump 10 configured for being implanted into a living body for pumping fluid 12, such as blood. For example, the pump may be configured as a Left Ventricular Assist Device (LVAD) surgically attached between the left atrium and descending aorta of a human heart. The pump includes a suitable inlet tube 10a at one end, and an outlet tube 10b at an opposite end for channeling the blood therethrough.

The pump is controlled by an electrical controller 14 suitably electrically joined thereto, and powered by a cooperating battery.

The pump includes a tubular housing 16 having a coaxial, smooth cylindrical center bore disposed in flow communication between a housing outlet and a first, aft end 16a thereof, and a housing inlet at an axially opposite, second or forward end 16b thereof.

A tubular rotor or piston 18 is disposed coaxially in the housing bore for axial translation and rotation therein. The piston includes a smooth center bore disposed in flow communication between a piston inlet and piston outlet at opposite axial ends thereof.

A first check valve 20a is fixedly joined in the housing inlet, and a second check value 20b is fixedly joined in the piston outlet in the exemplary configuration illustrated.

A linear motor 22 includes a plurality of axially adjoining, coaxial stator drive coils 22a disposed in the housing, which cooperate with a pair of axially spaced apart permanent magnet rings 22b disposed in the piston. The magnet rings are spaced radially inwardly of the drive coils for magnetically cooperating therewith to axially translate or oscillate the piston in the housing for cyclically pumping the blood therethrough in unidirectional flow, with the check valves preventing backflow.

The piston has a smaller diameter than the housing bore and is spaced radially inwardly therefrom to define a radial gap 24 therebetween for receiving and channeling a portion of the blood as a bearing fluid for hydrodynamically supporting the oscillatory piston as it rotates in the housing. The piston is entirely bathed in the blood during operation, and the piston gap effects a hydrodynamic journal bearing for suspending the piston with frictionless movement in the housing.

The linear motor 22 axially reciprocates the piston during operation. The piston may be additionally rotated during operation by various means. For example, an integral brushless DC rotary motor 26 may be incorporated in the linear motor 22 itself, although an independent rotary motor could otherwise be used. The rotary motor includes a pair of axially spaced apart stator bands 26a each having a plurality of circumferentially adjoining rotary-drive spin windings or coils disposed inside the housing, and radially below respective ones of the axial drive coils 22a.

Figure 2:
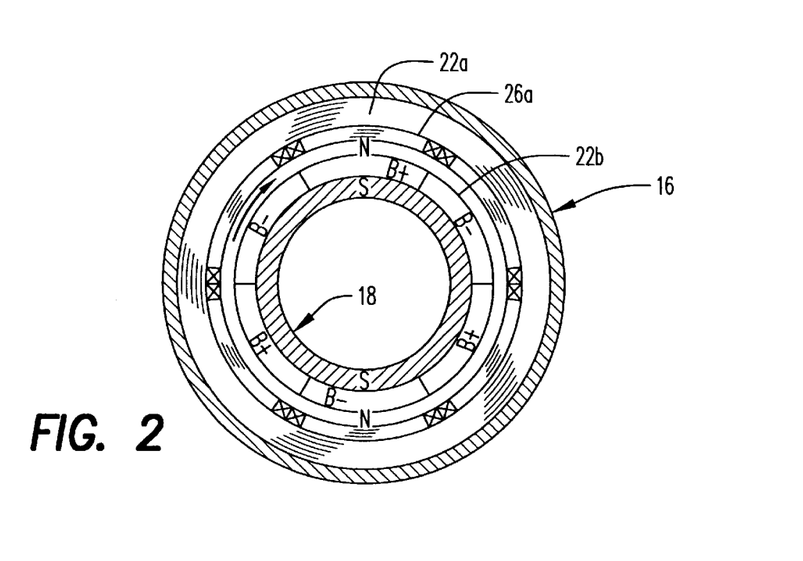
FIG. 2 is a radial sectional view through a portion of the linear pump illustrated in FIG. 1, and taken along line 2—2, showing a rotary motor therein.

As shown in more particularity in FIG. 2, the two magnet rings 22b have circumferentially spaced apart zones of different magnetic field flux density designated B+ and B−. This may be accomplished by slightly demagnetizing the circumferential zones around the perimeter of the magnet rings to create relatively high and low flux density zones for defining corresponding poles. The zones are axially in a common plane, and positioned radially below respective ones of the stator bands 26a for being magnetically rotated thereby. Each of the stator bands 26a as shown in FIG. 1 is disposed axially coextensively with a respective one of the symmetrical sets of three-drive coils 22a, and radially inwardly thereof for simultaneously axially translating and circumferentially rotating the piston in the housing.

The linear pump itself is described in more detail in the above-identified patent application and may have different configurations. For its particular use in pumping blood in a human patient, its components are preferably encapsulated in a suitable biocompatible material for reducing or preventing blood damage. For example, the housing and piston may be formed of titanium and suitably coated with a biocompatible material such as carbon if desired.

Operation of the linear motor 22 illustrated in FIG. 1 controls the axial reciprocation of the piston in the housing and the pumping action of the pump. Rotation of the piston in the housing maintains an effective journal bearing around the gap 24 for frictionless operation of the piston without undesirable damage to the blood.

Axial reciprocation requires suitable commutation of the axial drive coils 22a which are energized in sequence as the magnet rings 22b pass therebelow. In the previous embodiment of the linear pump described in the above identified application, a conventional magneto resistor position sensor was described for detecting axial position of the piston for use by the controller in commutating the drive coils. A subsequent improvement in the linear pump introduces a rotary encoder for detecting rotary movement of the piston for controlling its operation. A typical rotary encoder is a Hall effect magnetic field sensor cooperating with a magnetic field carried by the piston. However, the Hall sensor is incompatible with the magneto resistor sensor due to the different magnetic operations thereof.

Accordingly, instead of using the magneto resistor linear position sensor in the pump illustrated in FIG. 1, an ultrasonic linear position sensor is used which will not adversely affect operation of a conventional Hall effect rotary encoder (not shown). The ultrasonic linear position sensor includes a conventional ultrasonic transducer 28 suitably mounted at the first or aft end 16a of the housing for measuring ultrasonically the axial position of the piston in the housing for use in commuting the axial drive coils 22a.

Figure 3:
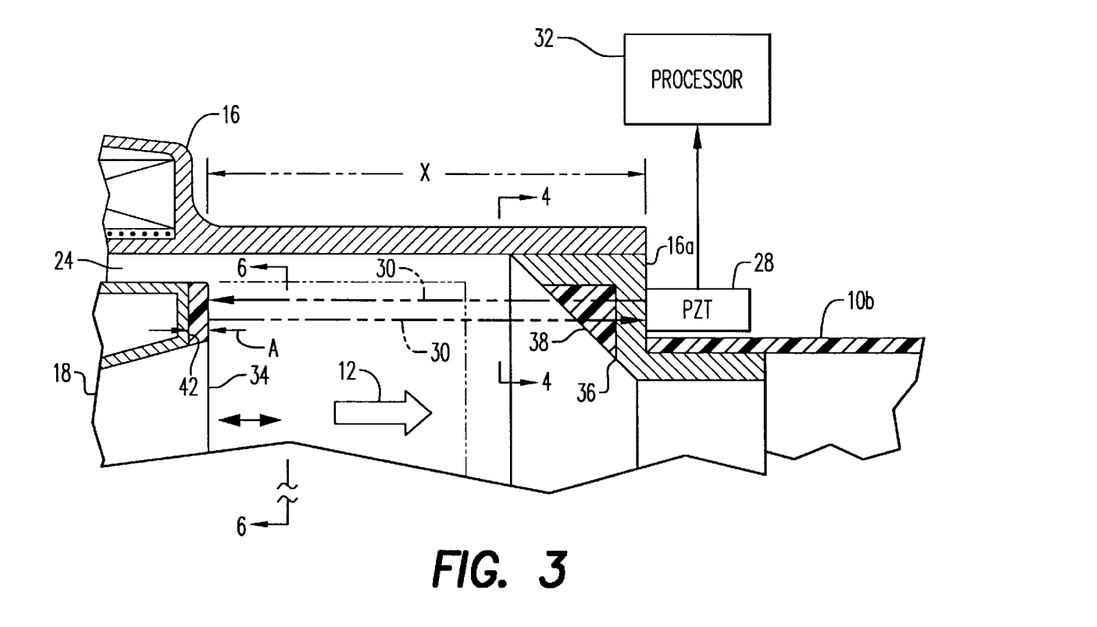
FIG. 3 is an enlarged, axial sectional view through the discharge end of the pump shown in FIG. 1 illustrating an exemplary embodiment of the linear position sensor.

FIG. 3 illustrates in more detail an exemplary embodiment of the transducer 28, which is also referred to as a piezoelectric transducer (PZT) which is effective for emitting ultrasonic pulses 30 at a suitable frequency, and simultaneously detecting return pulses, designated 30b, which are reflected back thereto. The transducer 28 is operatively joined to a suitable electrical processor 32 configured for providing an output signal representative of the axial position of the piston inside the housing. The processor 32 is in turn operatively joined to the controller 14, as illustrated in FIG. 1, for providing a closed loop control for commutating the axial drive coils 22a in a conventional manner.

Ultrasonic transducers are conventionally used as range finders for measuring distance between the transducer and a reflecting target. Distance is readily calculated by multiplying the speed of sound by half the round trip travel time between the emitted pulse and its returning echo.

However, accurate distance measurement requires an accurate value of the speed of sound in the travel medium. When such medium is blood, the speed of sound therein is subject to significant variation due to the inherent properties of blood and normal changes therein in a living body. Changes in the speed of sound in the blood fluid will introduce corresponding errors in position measurement using an ultrasonic transducer, such as the transducer 28 illustrated in FIG. 3. However, in accordance with the present invention, means are provided for periodically calibrating the speed of sound in the blood fluid 12 along the travel path of the pulses 30,30b.

More specifically, the piston 18 illustrated in FIG. 3 includes a target 34 at the first or aft end of the piston 18 which is radially aligned with the transducer 28 for reflecting the pulses 30 during operation. The transducer 28 is aimed at the target 34 which rotates with the piston during operation, and the target is perpendicular to the transducer for bouncing or reflecting back thereto the return pulses 30b along the path from which they came. The linear position of the target 34 is represented by the axial spacing X from the face of the transducer 28 to the target itself, which in turn determines the linear position of the piston inside the housing.

During operation, the transducer 28 emits the ultrasonic pulses 30 directed at the target 34 which are reflected therefrom as return pulses 30b which are detected by the transducer. The linear or axial position X of the target is then calculated by the product of the speed of sound in the blood 12 and half the round trip travel time of corresponding ultrasonic pulses.

The processor 32 may be in the exemplary form of a digitally programmable computer, or may be otherwise configured, to contain an initial, nominal value of the speed of sound for the intended fluid, such as blood. The output from the transducer, therefore, will provide a nominal position of the target subject to any inaccuracy in the value of the speed of sound therein. However, by self calibrating the speed of sound during operation, its value may be periodically updated in the processor for substantially improving the accuracy and providing long term stability of the measured linear position of the target.

The components of the linear position sensor may be used for both measuring linear position of the target during operation, as well as periodically calibrating the speed of sound in the blood in situ along the pulse path inside the housing during operation as the blood is being pumped.

The transducer 28 is mounted perpendicular to the target 34 for bouncing and detecting the ultrasonic pulses therefrom. However, in a blood pumping device, blood stagnation sites must be avoided for preventing blood damage and thrombosis during operation. As shown in FIG. 3, the transducer 28 may be suitably attached or bonded directly to a radial portion of the housing 16 which is parallel with the piston target 34. In this way, the ultrasonic pulses 30 may be directed perpendicularly from the housing end wall for bouncing off the flat target 34.

The thickness of the housing end wall is preferably about a quarter wavelength of the emitted pulses to provide constructive interference in the end wall for maximizing energy of the pulses transmitted therethrough. In this way, the transducer itself may be isolated from the blood flow inside the housing. The housing end wall is preferably beveled or inclined inside the housing for eliminating stagnation sites as the blood flows downstream therepast.

Figure 4:
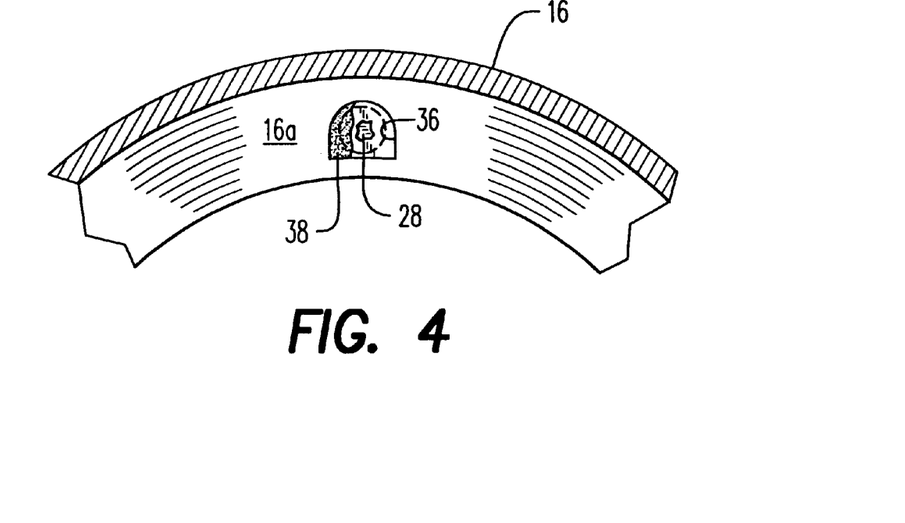
FIG. 4 is an aft facing elevational view of the housing end supporting the position transducer illustrated in FIG. 3 and taken along 4—4.

As shown in FIG. 4, the end wall at the housing aft end 16a preferably includes a contoured, or concave pocket 36 behind which the transducer 28 is aligned, with the pocket being empty if desired and providing a locally smooth transition for preventing blood stagnation at the origination site of the ultrasonic pulses. In a preferred embodiment, the pocket 36 may be filled with a suitable synthetic material 38, such as rubber, for filling the pocket to blend with the beveled housing end wall and eliminate blood stagnation sites. The blend material 38 has suitably low impedance to match that of blood so that the ultrasonic pulses may be transmitted directly therethrough without substantial energy loss. The rubber may be coated with carbon for blood compatibility.

Figure 5:
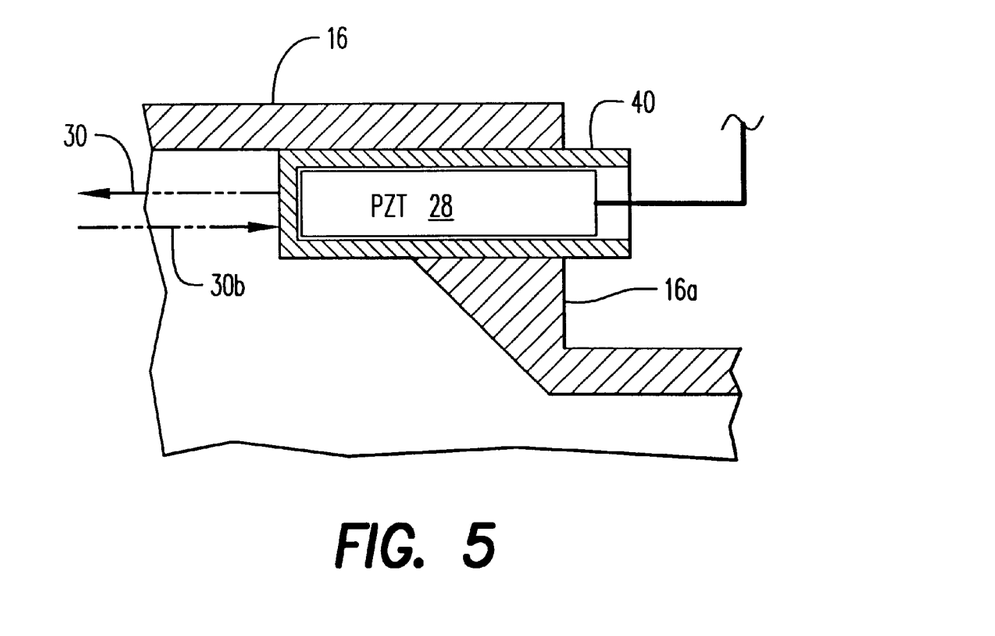
FIG. 5 is an enlarged, axial sectional view, like FIG. 3, illustrating an alternate embodiment of the position transducer.

As shown in FIG. 5, the transducer 28 may be mounted inside a tubular container 40, such as titanium, which projects through the beveled end wall of the housing. The container 40 has a flat distal end disposed inside the housing 16 which is parallel to the target 34 illustrated in FIG. 3 for permitting bouncing of the pulses 30 during operation. This configuration also avoids undesirable stagnation sites at the location of the transducer 28 while permitting its alignment with the intended target 34.

Self calibration of the linear position sensor illustrated in FIG. 3 is effected by providing a calibration feature of the piston 18 having a predetermined or known calibration dimension relative to the target 34. By providing a known calibration dimension, the transducer 28 may be operated for bouncing the pulses through the blood 12 and off the target 34 to measure the linear position thereof. The processor 32 may then be used for calculating the speed of sound in the blood based on the instantaneous position of the target, the known calibration dimension, and measured round trip times of the pulses.

Figure 6:
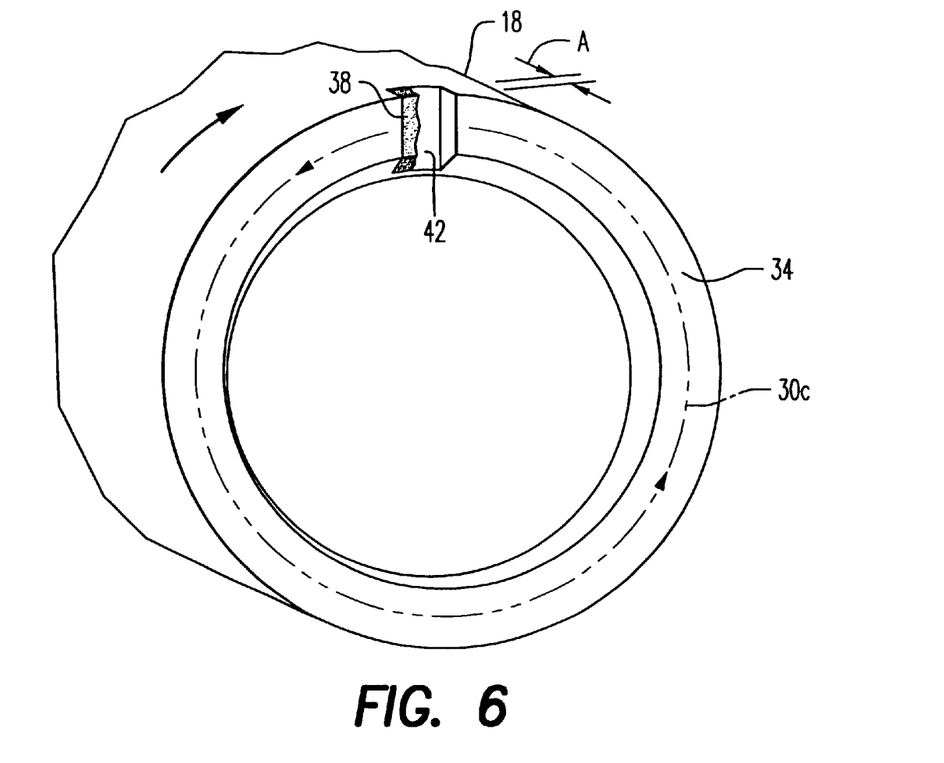
FIG. 6 is an isometric end view of the aft end of the piston shown in FIG. 3 and taken along line 6—6 illustrating a slotted step in an end face cooperating with the position transducer.

As shown in FIGS. 3 and 6, the piston rotor is tubular with an open center bore. The target 34 is preferably the flat annulus or land defined at the aft end of the piston. The target 34 is configured to face the transducer 28 for receiving the pulses 30 perpendicularly therefrom so that they may be reflected along the same path from which they came. Since the piston 18 rotates during operation, as illustrated in FIG. 6, the emitted pulses 30 from the stationary transducer will follow a circular path, designated 30c, around the target 34 as it rotates as part of the piston. In this way, the linear position of the piston may be continuously measured as the piston reciprocates and rotates, and the pulses are reflected from the target.

In the exemplary embodiment illustrated in FIGS. 3 and 6, the calibration feature is a local step 42 in the exemplary form of a slot or notch formed in a circumferential portion of the target. As shown in FIG. 6, a single step 42 may be formed in the perimeter of the target and extends axially inwardly therefrom. The corresponding calibration dimension is the axial offset A of the step from the plane of the target 34. If desired, the step slot 42 may be completely filled with the low impedance blend material 38 for providing a smooth surface to prevent blood stagnation.

During operation, the ultrasonic pulses are bounced in turn off the annular target 34 and the interrupting step 42 therein as the piston rotates and translates inside the housing. The transducer not only measures the linear position of the target 34 as the piston moves, but also measures the position of the step 42 itself intermittently as the piston rotates. Since the calibration dimension A is a precisely known value, the processor is configured for periodically self calibrating the speed of sound during operation.

This is accomplished by calculating the speed of sound from the differences in round trip travel times of the pulses as they bounce off the corresponding linear positions of the target and step which are different by the known calibration offset. The calculated speed of sound is simply the calibration dimension A divided by half the difference in round trip travel times of the pulses between the target and the step.

For example, the calibration dimension A may be about 50 mils (1.27 mm) which can be measured ultrasonically to an accuracy of about 1%. A larger calibration dimension will provide greater accuracy if desired. The circumferential width of the step 42 may have any suitable value and may be as little as that of the corresponding width of the ultrasonic pulses to ensure independent and distinct reflection pulses between the step and the target for discriminating the transition therebetween and the calibration dimension A.

Accordingly, the speed of sound in the blood may be self calibrated each time the transducer detects the transition and return signal between the step and target, which is substantially instantaneous.

Figure 7:
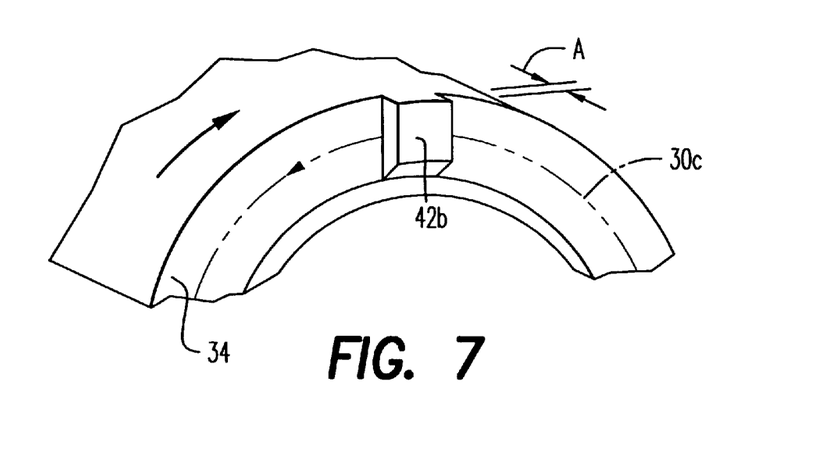
FIG. 7 is an isometric, end view, like FIG. 6, of the piston illustrated in FIG. 3 in accordance with an alternate embodiment of the present invention having a pad step cooperating with the end face target.

FIG. 7 illustrates an alternate embodiment of the step in the form of an elevated or raised pad designated 42b extending axially outwardly from the remainder of the target 34, with a corresponding calibration dimension A. The ultrasonic pulses are bounced off the step pad 42b in the same manner as they are bounced off the step slot 42 illustrated in FIG. 6 to provide a sharp change in round trip travel times indicative of the target-to-step transition as the piston rotates during operation. The speed of sound may then be calculated by the processor by dividing the known calibration dimension A by half the difference in the round trip travel times of the pulses bouncing off the pad 42b and the adjacent target 34.

In the exemplary embodiment illustrated in FIGS. 6 and 7, the calibration dimension corresponds with a local discontinuity in the target 34 at the aft end of the piston. However, the calibration dimension may be the entire axial length of the piston 18 illustrated in FIG. 1, with the target 34 remaining uninterrupted around its perimeter, in another embodiment.

In this embodiment, the calibration feature may be the entire upstream or forward end face 18b of the piston at the second axial end thereof opposite to the target 34. The forward end face 18b may be identical in configuration to the annular target 34 at the opposite end of the piston. The calibration dimension is then the entire axial length of the rotor between its two end faces.

In this embodiment, the controller 14 may be used during the calibration process to temporarily hold the piston 18 at its forward end against the upstream end of the housing 16. The piston end face 18b is thusly temporarily seated against the upstream housing second end 16b, and the transducer 28 is operated for bouncing the ultrasonic pulses off the target 34 at the opposite end of the housing for measuring the target position.

Since the length of the piston between the target 34 and its upstream end face 18b is precisely known, and since the length of the housing 16 from the point of piston seating and the transducer 28 is also precisely known, the difference therebetween representing the axial linear position of the target 34 is also precisely known when the piston is seated. Accordingly, the speed of sound in the blood may be calculated based on this target position and half the round trip travel time of the corresponding ultrasonic pulses. The speed of sound is simply the known linear position of the target 34 while the piston is seated in the housing divided by the pulse travel time from the transducer to the target.

Although this method of calibrating the speed of sound requires temporary seating of the piston at the forward end of the housing, that seating may be effected almost instantaneously without adversely affecting the pumping requirements of the linear pump. In such an embodiment, it is preferred to incorporate a small conical stop (not shown) extending axially aft from the housing second end 16b against which the piston end face 18b may abut during the calibration process. In this way a single point of contact is provided between the housing and the piston for minimizing any contact damage to the blood flowing therebetween.

Instead of temporarily seating the piston in the housing as indicated above, the calibration length of the piston may be used in another method for self calibrating the speed of sound. In this embodiment, also illustrated in FIG. 1, the calibrating means further include a second one of the ultrasonic transducers, designated 28b, suitably mounted at the housing second end 16b opposite to its first end 16a in which the first transducer 28 is mounted. The second transducer 28b is aligned with the rotor end face 18b and is operatively joined to the processor 32.

Both transducers 28,28b may be simultaneously operated for bouncing corresponding ultrasonic pulses off both the target 34 at one end of the piston 18, and off the end face 18b at the opposite end of the piston to measure respective linear positions thereof. The processor 32 may then be configured for calculating the speed of sound in the blood based on the respective linear positions of the target 34 and end face 18b, the rotor axial length therebetween, and the respective round trip travel times of the ultrasonic pulses.

Since the length of the housing between the two transducers is precisely known, and the length of the rotor is precisely known, the sum of the respective linear positions of the target 34 and end face 18b is a precise constant. The speed of sound may therefore be calculated by dividing that constant sum by half the sum of the round trip travel times between the respective transducers and their targets.

In the various embodiments disclosed above, one or more ultrasonic transducers may be used for precisely measuring the axial linear position of the piston reciprocating in the housing for use in commutating the axial drive coils. The speed of sound in the fluid may be periodically self calibrated using the same transducer and the processor 32 for increasing the accuracy of linear position measurement even as the speed of sound changes during operation of the pump. If desired, a Hall effect rotary encoder may be used in conjunction with the position transducer without interference therewith.

In accordance with another embodiment of the present invention, the same ultrasonic transducer 28 may be used for not only measuring linear position of the rotor, but for also effecting a rotary encoder for measuring rotary movement of the piston which may then be used with the controller for controlling both axial reciprocation and rotation of the piston.

Figure 8:
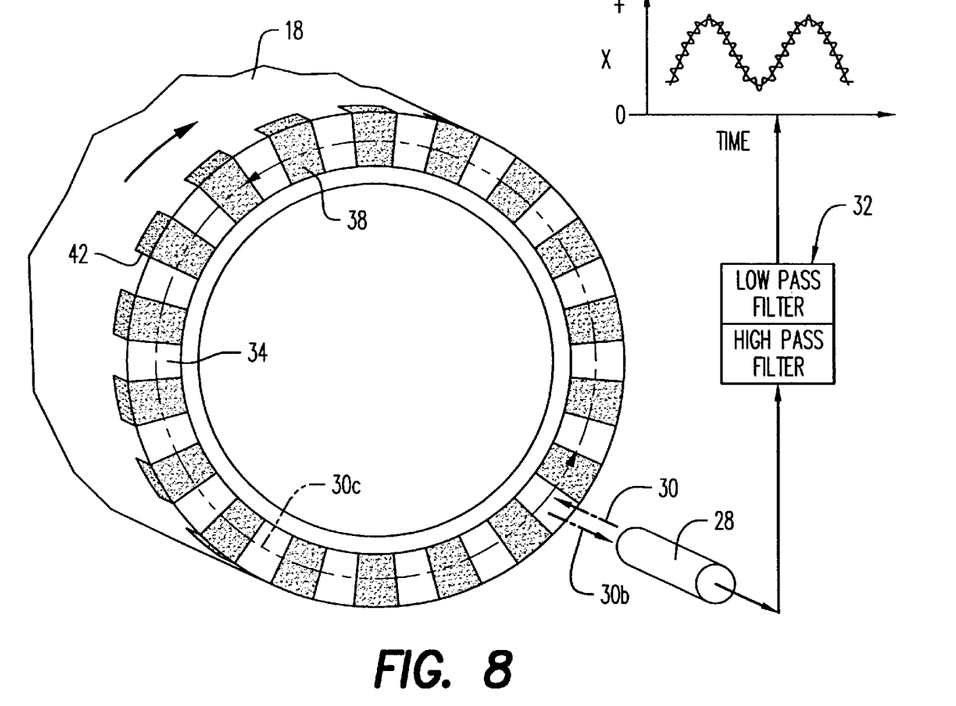
FIG. 8 is an isometric end view, like FIG. 6, of the piston illustrated in FIG. 3 in accordance with another embodiment of the present invention having a plurality of circumferentially spaced apart steps and targets.

In the exemplary embodiment illustrated in FIG. 8, the calibration feature includes a plurality of the steps 42 circumferentially spaced apart from each other around the target 34. The individual steps 42 may be in the form of the radial slot or notch illustrated in FIG. 6 with or without the blend material 38 disposed therein. Alternatively, the steps 42 illustrated in FIG. 8 may be in the form of the elevated pads 42b illustrated in FIG. 7.

In either embodiment, the steps 42,42b have the predetermined calibration dimension A relative to the target which permits not only self calibration of the speed of sound in the blood, but also rotary encoding.

For example, tests have shown that a 10 MHz frequency of the ultrasonic pulses generated by the transducer 28 is effective for propagation through blood without significant attenuation or blood damage. However, a 5 MHz ultrasonic frequency resulted in undesirable attenuation in blood. Ultrasonic frequencies greater than 5 MHz are therefore desired for use in a blood pump, although other frequencies may be used for different liquids other than blood.

A typical operation of the blood pump 10 may include axial reciprocation of the piston up to about 8 Hz, with a corresponding rotary speed of the piston of about 300 rpm. In the exemplary embodiment illustrated in FIG. 8, eighteen steps 42 are provided with eighteen portions of the target 34 alternating therebetween for rotary encoding. The circumferential widths of the steps 42 are preferably equal to each other, and the circumferential widths of the target portions are equal to each other. And, the widths of the steps and targets may be equal to each other for providing 36 arcuate portions of 10° each.

Accordingly, as the piston 18 rotates at 5 Hz during operation, the eighteen steps 42 rotating past the transducer 28 effect a nominal frequency of 90 Hz for a rotary encoded signal. The transducer 28 therefore detects both the linear position of the reciprocating piston up to about 8 Hz, and the rotary motion of the piston at about 90 Hz.

Shown schematically in FIG. 8 is a graph of axial linear position X of the piston as it reciprocates over time with the frequency up to about 8 Hz, upon which is superimposed the 90 Hz rotary signal. Since the target 34 illustrated in FIG. 8 is co-radial with the steps 42 in a common radial annulus, the steps circumferentially interrupt the target into corresponding portions. And, the transducer 28 is aligned with the piston 18 to intercept the steps and target portions in turn as the rotor rotates. The transducer 28 therefore provides a common detection signal including components for both the axial position of the piston and its rotary motion. The processor 32 is correspondingly configured for calculating the linear position of the target 34 based on the round trip times of the ultrasonic pulses transmitted from the transducer, and resolving rotary motion of the rotor based on changes in the round trip pulse times from step to target portion circumferentially around the piston.

For example, the processor 32 may include a low pass filter for a frequency range of about 2–8 Hz for resolving the target linear position, and a high pass filter in the exemplary range of 70–120 Hz for resolving the rotary motion. By so filtering the signal from the transducer 28, both linear position and rotary motion of the piston may be determined and provided to the controller for operating the pump.

The separation of these two frequency bands is about 10:1, effected by selecting the eighteen steps 42, which is suitable for separately resolving linear from rotary motion. The rotary motion may include the rotary speed of the piston, as well as the angular rotary position thereof obtained by counting the individual steps 42 as distinguished by the signal changes in the transducer from step-to-target.

The apparatus illustrated in FIG. 8 requires corresponding signal processing to filter out the axial and rotary signals from the combined signal from the transducer 28. This increases complexity and cost of the processor. However, the processor may be simplified by decoupling the axial and rotary signals.

Figure 9:
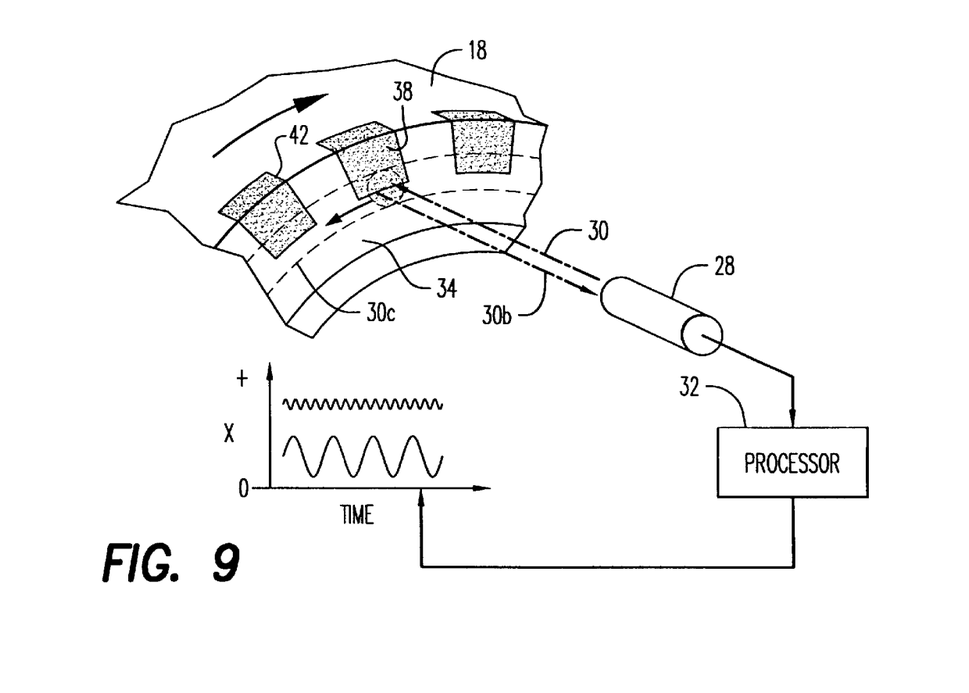
FIG. 9 is an isometric end view, like FIG. 8, of the piston end in accordance with another embodiment of the present invention with an annular target adjoining the spaced apart steps.

More specifically, FIG. 9 illustrates an alternate embodiment of the invention wherein the processor 32 is configured to resolve the linear position and rotary motion of the piston 18 without filtering therefor. In this embodiment, the target 34 is a continuous annulus disposed radially inwardly of the steps 42, and the transducer 28 is aligned with the piston to intercept the steps 42 and target 34 in respective parts as the piston rotates.

As shown in FIG. 9, the ultrasonic pulses 30 have an effective diameter of impact sufficiently large for bridging in part the target 34 and respective ones of the steps 42 over an annular band therebetween. In this way, the same pulses 30 may be bounced in part off the target 34 and in part off the steps 42 in turn so that the reflected pulses 30b include discrete portions corresponding to the target and steps at different axial positions with correspondingly different round trip travel times.

The linear position and rotary motion of the piston may therefore be resolved independently without filtering. The reflected pulses 30b provide two simultaneous components indicative of the respective linear positions of the target and steps, with the signal component for the steps having a frequency corresponding to the rotary speed of the piston and the multiple number of steps, which is different than the substantially lower reciprocation frequency of the piston. The graph illustrated in FIG. 9 is a schematic representation of the simultaneous processing of the common transducer signal to include the low frequency axial position component and the higher frequency rotary motion component corresponding to those superimposed in FIG. 8.

The self calibrating linear position sensor disclosed above, including the ultrasonic transducer 28 and its cooperating processor 32, are provided for the exemplary embodiment of the linear blood pump 10 in which the speed of sound therein can vary significantly over time. The processor 32 illustrated in FIG. 1 is operatively joined to the controller 14, which in turn controls the linear motor 22 and axial reciprocation of the piston, while also controlling the rotary motor 26 and the rotary motion of the piston including its rotary speed.

Pumping of the blood through the piston 18 during operation may therefore be precisely controlled notwithstanding changes in the speed of sound through the blood. The transducer 28 may be used for measuring linear position of the piston, with a corresponding Hall effect rotary encoder being used for monitoring rotary motion of the piston without interference with the transducer 28. Or, the transducer and processor may be configured with the particular embodiment of the target and steps illustrated in FIGS. 8 and 9 for providing measurement of both linear position and rotary motion of the piston in one measuring device.

The self calibrating linear position sensor disclosed above may be used in alternate applications wherever the axial and/or rotary position of a rotor suspended within a fluid-filled housing is desired. For example, magnetic bearings are known for magnetically supporting a shaft in a housing in an exemplary rotor pump. The shaft supports a centrifugal pump impeller which requires precise centering in its housing (not shown). By incorporating the self calibrating linear position sensor disclosed above at the end of the magnetically supported shaft, its linear position may be precisely determined for controlling its position within the housing.

While there have been described herein what are considered to be preferred and exemplary embodiments of the present invention, other modifications of the invention shall be apparent to those skilled in the art from the teachings herein, and it is, therefore, desired to be secured in the appended claims all such modifications as fall within the true spirit and scope of the invention.

Accordingly, what is desired to be secured by Letters Patent of the United States is the invention as defined and differentiated in the following claims in which I claim:

1. An apparatus comprising:

a tubular housing;

a rotor disposed coaxially in said housing and spaced radially inwardly therefrom to define a gap therebetween for receiving a fluid, and including a target at one end thereof;

an ultrasonic transducer mounted at a first end of said housing in alignment with said target for bouncing ultrasonic pulses thereoff for measuring linear position thereof based on the speed of sound in said fluid and the round trip pulse time between said transducer and target; and means for calibrating said speed of sound in said fluid from a predetermined calibration dimension between said transducer and target.

2. An apparatus according to claim 1 wherein calibrating means comprise:

a feature of said rotor having said predetermined calibration dimension relative to said target; and a processor operatively joined to said transducer for calculating said speed of sound in said fluid based on said target position, said calibration dimension, and said round trip pulse time.

3. An apparatus according to claim 2 wherein:

said calibration feature comprises an end face of said rotor at an axial second end thereof opposite to said target, with said calibration dimension being axial length of said rotor therebetween; and said calibrating means are configured to hold said rotor end face at a corresponding opposite second end of said housing for measuring said linear position of said target by said transducer.

4. An apparatus according to claim 2 wherein:

said calibration feature comprises an end face of said rotor at an axial second end thereof opposite to said target, with said calibration dimension being axial length of said rotor therebetween;

said calibrating means further comprise a second ultrasonic transducer operatively joined to said processor opposite to said first transducer in alignment with said rotor end face for bouncing second ultrasonic pulses thereoff for measuring linear position thereof; and said processor is configured for calculating said speed of sound in said fluid based on said positions of said rotor target and end face, said rotor axial length, and said respective round trip pulse times.

5. An apparatus according to claim 2 wherein:

said target comprises a flat annulus at said rotor first end; and said calibrating feature is a local step in said target, and said calibration dimension is axial offset of said step from said target.

6. An apparatus according to claim 5 wherein said calibration feature comprises a plurality of said steps circumferentially spaced apart from each other around said target.

7. An apparatus according to claim 6 wherein said steps comprise pads extending axially outwardly from said target.

8. An apparatus according to claim 6 wherein said steps comprise slots extending axially inwardly from said target.

9. An apparatus according to claim 6 wherein said processor is configured for calculating said linear position of said target based on said round trip times of said pulses transmitted from said transducer, and resolving rotary motion of said rotor based on changes in said round trip pulse times circumferentially around said steps.

10. An apparatus according to claim 9 further comprising:

means for axially reciprocating said rotor inside said housing; and means for rotating said rotor inside said housing.

11. An apparatus according to claim 10 wherein:

said target is co-radial with said steps and circumferentially interrupted thereby; and said transducer is aligned with said rotor to intercept said steps and target in turn as said rotor rotates.

12. An apparatus according to claim 11 wherein said processor includes a low pass filter for resolving said target linear position from said transducer, and a high pass filter for resolving said rotary motion from said transducer.

13. An apparatus according to claim 10 wherein:

said target is a continuous annulus disposed radially inwardly of said steps; and said transducer is aligned with said rotor to intercept said steps and target each in part as said rotor rotates.

14. An apparatus according to claim 13 wherein said processor is configured to resolve said linear position and rotary motion from said transducer without filtering therefor.

15. An apparatus according to claim 10 wherein: said rotor comprises a piston for pumping blood fluid through said housing; and said processor is operatively joined to said reciprocating and rotating means for controlling movement of said piston and flow of said blood through said housing.

16. A method of measuring linear position of a rotor disposed inside a housing in a fluid comprising:

bouncing from said housing ultrasonic pulses off a target at a first end of said rotor and through said fluid for measuring linear position of said target in said housing based on the product of speed of sound in said fluid and round trip times of said bounced pulses along a pulse path between said housing and target; and calibrating said speed of sound in said fluid from a predetermined calibration dimension along said pulse path.

17. A method according to claim 16 wherein said speed of sound calibration comprises:

providing said predetermined calibration dimension in said rotor relative to said target;

bouncing said pulses through said fluid and off said target to measure said linear position thereof; and calculating said speed of sound in said fluid based on said target position, said calibration dimension, and said round trip pulse time.

18. A method according to claim 17 wherein said speed of sound calibration further comprises:

holding said rotor at one end of said housing;

bouncing said pulse off said target at an opposite end of said housing for measuring said target position; and calculating said speed of sound in said fluid based on said target position and said round trip pulse time.

19. A method according to claim 17 wherein said speed of sound calibration further comprises:

bouncing corresponding ultrasonic pulses off both said target at one end of said rotor, and off an end face at an opposite end of said rotor to obtain respective round trip times thereof; and calculating said speed of sound in said fluid based on linear positions of said target and end face, and said respective round trip pulse times.

20. A method according to claim 17 further comprising:

providing a local step in said target to define said calibration dimension therebetween;

bouncing said pulses in turn off said target and step as said rotor rotates and translates inside said housing for measuring linear positions thereof; and calibrating said speed of sound from the difference in round trip pulse times between the linear positions of said target and step.

21. A method according to claim 20 further comprising:

providing a plurality of said steps circumferentially spaced apart from each other around said target;

bouncing said pulses off said target and steps as said rotor rotates and translates inside said housing 16 for measuring linear positions thereof; and resolving rotary motion of said rotor based on changes in said round trip pulse times circumferentially around said steps.

22. A method according to claim 21 wherein:

said pulses are bounced off said target and steps in turn as said rotor rotates; and said linear position and rotary motion of said rotor are resolved by filtering said pulses bounced from said target and steps.

23. A method according to claim 21 wherein:

said pulses are bounced in part off said target and in part off said steps in turn; and said linear position and rotary motion of said rotor are resolved independently.

* * * * *